United States Patent [19]

Nakajima et al.

[11] Patent Number: 5,036,072
[45] Date of Patent: Jul. 30, 1991

[54] ANTIVIRAL AGENT

[75] Inventors: Tsunetaka Nakajima; Tadao Okamoto; Masahiro Watanabe; Kazumasa Yokoyama, all of Hirakata, Japan

[73] Assignee: Ishihara Sangyo Kaisha Ltd., Osaka, Japan

[21] Appl. No.: 469,052

[22] Filed: Jan. 23, 1990

[30] Foreign Application Priority Data

Jan. 24, 1989 [JP]  Japan .................................. 1-15624

[51] Int. Cl.$^5$ ........................................... A61K 31/505
[52] U.S. Cl. ..................... 514/274; 514/351; 514/346
[58] Field of Search ................. 514/274, 351, 346

[56] References Cited

U.S. PATENT DOCUMENTS 4,173,638 11/1979 Nishiyama et al. ............... 424/263
4,344,951 8/1982 Nishiyama et al. ............... 424/263
4,798,839 1/1989 Ayad ............................... 514/351

FOREIGN PATENT DOCUMENTS 0192263 2/1986 European Pat. Off.
0262560 4/1988 European Pat. Off.
7109721 12/1980 Japan.

OTHER PUBLICATIONS

Patent Abstracts of Japan, vol. 12, no. 37 (C-473) [2884], 4th Feb. 1988; & JP-A-62 185 013 (Green Cross Corp 13-08-1987 *Whole Abstract*.

Primary Examiner—Frederick E. Waddell
Assistant Examiner—Russell Travers
Attorney, Agent, or Firm—Oblon, Spivak, McClelland, Maier & Neustadt

[57] ABSTRACT

Use of a benzoyl urea compound of the formula:

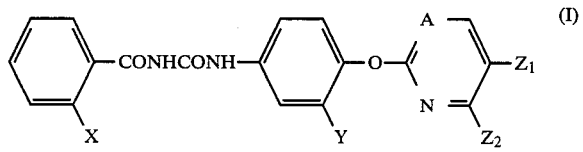

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is CH or a nitrogen atom, as an antiviral agent.

8 Claims, No Drawings

ANTIVIRAL AGENT

The present invention relates to an antiviral agent. More particularly, the present invention relates to novel use of a benzoyl urea compound having a specific chemical structure, as an antiviral agent.

Heretofore, a benzoyl urea compound represented by the following formula I is per se known:

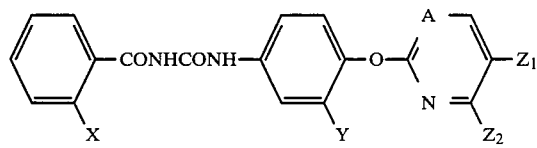
(I)

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is CH or a nitrogen atom.

Further, it is known that such a benzoyl urea compound shows an excellent antitumorous action (e.g. Japanese Unexamined Patent Publications No. 109721/1982, No. 1670/1986, No. 93163/1986 and No. 205257/1986).

The object of the present invention is to provide novel use of the benzoyl urea compound I.

From further studies of the phamacological actions of the benzoyl urea compound I, the present inventors have found that this compound has an excellent antiviral action. The present invention has been accomplished based on this discovery.

Namely the present invention provides use of a benzoyl urea compound of the formula:

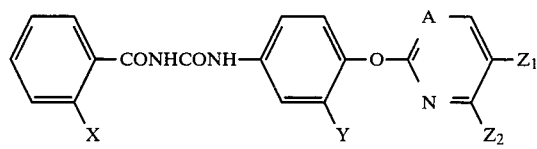
(I)

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is CH or a nitrogen atom, as an antiviral agent.

Now, the present invention will be described in detail with reference to the preferred embodiments.

In the formula I, the halogen atom includes chlorine, bromine and iodine.

The benzoyl urea compound I as the antiviral agent of the present invention includes, for example, compounds of the following formulas:

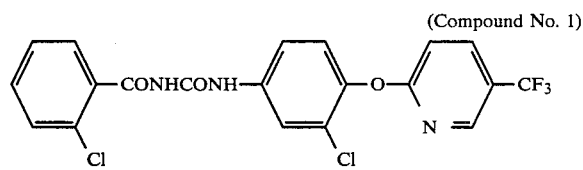
(Compound No. 1)

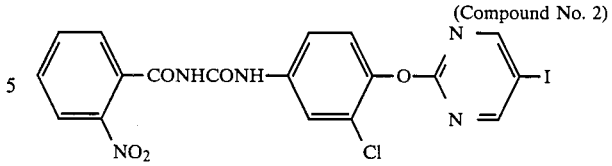
(Compound No. 2)

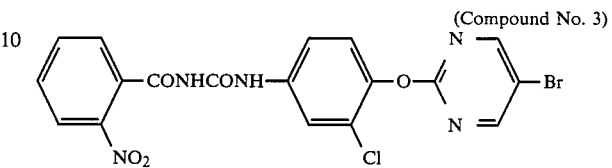
(Compound No. 3)

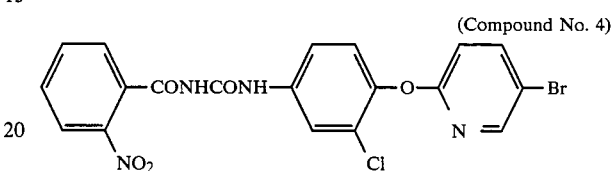
(Compound No. 4)

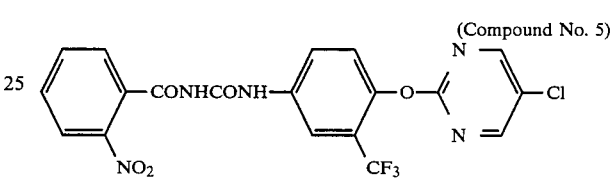
(Compound No. 5)

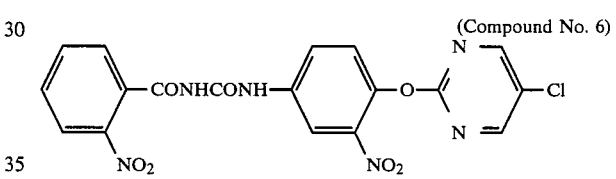
(Compound No. 6)

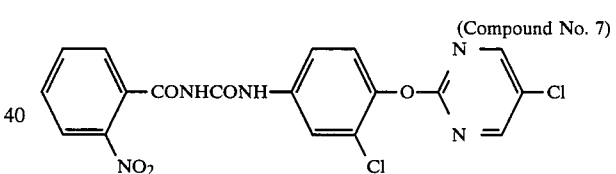
(Compound No. 7)

The benzoyl urea compound I is per se known and can be produced by the method described in Japanese Unexamined Patent Publication No. 109721/1982 or by a method similar thereto.

The benzoyl urea compound I is generally hardly soluble in water and accordingly inferior in the absorbability to blood. Therefore, various expedients for its formulation have been proposed (Japanese Unexamined Patent Publications No. 27965/1986, No. 191623/1986, No. 205257/1986 and No. 185013/1987, and European Unexamined Patent Publication No. 264904).

Specifically, an antiviral composition of the present invention is preferably formulated in the following manner.

Namely, a preferred formulation of the antiviral composition of the present invention can be prepared by pulverizing the benzoyl urea compound I in an aqueous suspension containing a dispersant, then adding a disintegrant thereto, and lyophilizing the mixture.

When used for the preparation of the antiviral composition of the present invention, the benzoyl urea compound I is preferably as fine as possible.

The dispersant serves as a dispersing agent when the benzoyl urea compound I is suspended and pulverized in water. A nonionic surfactant may be used as the dispersant without any particular limitation so long as the object of the present invention can thereby be attained, and it can be used as a pharmaceutically acceptable additive. Particularly preferred is the one in which the hydrophile-lipophile balance is more than 3. Specific examples of such a dispersant include a polyoxyethylene hardened castor oil, a polyoxyethylene polyoxypropylene glycol, a sugar fatty acid ester, a glycerine fatty acid ester, a sorbitan fatty acid ester, a propylene glycol fatty acid ester, a polyglycerine fatty acid ester, a polyoxyethylene sorbitan fatty acid ester, a polyoxyethylene sorbit fatty acid ester, a polyoxyethylene glycerine fatty acid ester, a polyethylene glycol fatty acid ester and a polyoxyethylene castor oil. Among these nonionic surfactants, preferred are the polyoxyethylene hardened castor oil, the polyoxyethylene polyoxypropylene glycol and the polyglycerine fatty acid ester.

The disintegrant is incorporated primarily to enhance the granularity and disintegrantability at the time of lyophilizing the benzoyl urea compound I.

As such a disintegrant, there may be mentioned a sugar, a sugar alcohol, an anhydrous silicic acid and a nonionic surfactant.

As the sugar for the disintegrant, there may be mentioned a monosaccharide (such as glucose or fructose), a disaccharide (such as sucrose, maltose or lactose) and a polysaccharide (such as starch, dextrin or cellulose).

As the sugar alcohol for the disintegrant, there may be mentioned a mannitol and a sorbitol.

As the anhydrous silicic acid for the disintegrant, a light anhydrous silicic acid may be mentioned.

The nonionic surfactant useful as the disintegrant includes, for example, a polyoxyethylene hardened castor oil, a polyoxyethylene polyoxypropylene glycol, a sucrose fatty acid ester, a glycerine fatty acid ester, a sorbitan fatty acid ester, a propylene glycol fatty acid ester, a polyglycerine fatty acid ester, a polyoxyethylene sorbitan fatty acid ester, a polyoxyethylene sorbit fatty acid ester, a polyoxyethylene glycerine fatty acid ester, a polyethylene glycol fatty acid ester and a polyoxyethylene castor oil.

The nonionic surfactant is preferably used as the disintegrant. Particularly preferred is the sucrose fatty acid ester or polyoxyethylene polyoxypropylene glycol.

Although the same nonionic surfactant may be used both as the dispersant and as the disintegrant, different ones are preferably used. For example, when the polyglycerine fatty acid ester (e.g. decaglycerine monolaurate) or the polyoxyethylene hardened castor oil (e.g. polyoxyethylene hardened castor oil 60) is used as the dispersant, it is preferred to use the sucrose fatty acid ester as the disintegrant.

The pulverization of the benzoyl urea compound I in the aqueous suspension containing the dispersant is carried out preferably in a wet system. The pulverization in a wet system is a method wherein the material to be pulverized is rotated or shaked together with beads (particularly glass beads) in the liquid containing a dispersant. A machine such as Dino-mill (KDL type, made by Willy A Bachofen Company) may be used for the method. At the time of the pulverization, the concentration of the bezoyl urea compound I in the aqueous suspension is from 1 to 70%, preferably from 20 to 50%, by weight/volume. The concentration in such a range is preferable particularly when Dino-mill is used for pulverization in a wet system. The concentration of a non- ionic surfactant as the dispersant is from 1 to 30%, preferably from 2 to 20%, by weight/volume. The diameter of the glass beads to be used, is usually in a range of from 0.1 to 1.5 mm, preferably from 0.25 to 0.5 mm. The pulverization time is usually in a range of from 5 to 60 minutes. The benzoyl urea compound I which has been pulverized in a wet system by using the above mentioned conditions, has a mean granular diameter of from 0.2 to 1.0 $\mu$m (as measured by a photo scattering method).

After the pulverization in a wet system, the glass beads are removed by a sieve. The disintegrant is then added to the liquid of the pulverized benzoyl urea compound I, followed by lyophilization. The concentration of the dipersant is in a range of from 1 to 90%, preferably from 10 to 70%, by weight/volume.

The above formulation, particularly the freeze-dried formulation, of the antiviral composition of the present invention, preferably has a composition by a weight ratio of e.g. benzoyl urea compound I:dispersant:disintegrant = 1 to 70:1 to 30:1 to 90, preferably 20 to 50:2 to 20:10 to 70.

The formulation, particularly the freeze-dried formulation of the present invention can further be formed into various optional formulations by conventional methods. Such optional formulations include, for example, formulations for oral administration such as powders, microgranules, granules, capsules, tablets and liquid formulations, and formulations for intrarectal administration such as suppositories.

The antiviral agent of the present invention shows excellent antiviral activities when applied to mammals (such as human beings, horses, cattle, dogs, mice and rats).

The antiviral agent of the present invention is effective particularly for the treatment of an infection by herpesvirus (particularly herpes simplex), varicella zoster, cytomegalovirus (CMV) or Epstein-Barr virus (EBV). Further, the antiviral agent of the present invention can be effectively used for the treatment of an infection by picornavirus, togavirus such as arbovirus, retrovirus (such as leucovirus), arenavirus, coronavirus, rhabdovirus, paramyxovirus, non-A-typed hepatitis virus, non-B-typed hepatitis virus, iridovirus, papovavirus, parvovirus, reovirus or bunyavirus.

Another area to which the antiviral agent of the present invention can be applied, is the treatment of a cancer or tumor caused by virus. Such an effect is obtainable by various mechanisms, i.e. by controlling the conversion of the virus-infected cells to a neoplasm state, by controlling the diffusion of the virus from the converted cells to other normal cells, and by preventing the growth of cells converted by virus.

A further area to which the antiviral agent of the present invention can be applied in connection with cancer chemotherapy, is the treatment of multiple myeloma and cancers of lung (and trachea), stomach, liver, colon, bladder, lip, bone, ren, ovarium, prostate, pancreas, skin (melanoma), rectum, sialaden, mouth, esophagus, orchis, encephalon (and craniomeninx), thyroid gland, gallbladder (and cystic duct), nose, pharynx, connective tissue, penis, cunnus, vagina, body of uterus, tongue, breast and cervical duct.

The antiviral agent of the present invention is usually orally administered to mammals including human, cattle, horses, dogs, rats and mice. However, it is possible to administer it by other administration route such as intrarectal administration. The dose may vary depending upon e.g. the diseased state, the sex, the body weight and the type of formulation. However, in the case of oral administration, a daily dose of the benzoyl urea compound I for an adult is from 1 to 100 mg/kg body weight, and such a dose is administered from once to third times per week.

The benzoyl urea compound I as the active ingredient of the antiviral composition of the present invention, is a compound having a structure which is entirely different from conventional antiviral agents. Thus, the antiviral agent of the present invention is extreamly useful as a novel pharmaceutical product.

TEST EXAMPLE 1

The antiviral activities were evaluated by a plaque-reduction evaluation method. Verocells were inoculated to a plastic Petri dish and then proliferated until they formed a monolayer. To each Petri dish, a predetermined number of plaque-forming units (about 100 to 500) of helpes simplex virus (1-type, KOS strain) were infected. Compound 3 was dissolved in 2% of bovine fetus serum inactivated by heating and adjusted to a predetermined concentration. One hour after the infection, the drug solution was added to the cultivation Petri dish (8 ml/Petri dish). Three days later, the cultivation Petri dish was fixed by formalin and dyed with Crystal Violet, whereupon the number of plaques was counted. The results are shown in Table 1.

TABLE 1

| Drug | Concentration (μg/ml) | Number of plaques | Inhibition (%) |
| --- | --- | --- | --- |
| Compound 3 | 1 | 264.5 | 45.1 |
| Compound 3 | 2.5 | 122.0 | 74.7 |
| Compound 3 | 5 | 27.5 | 94.3 |
| Nil | 0 | 482 | — |

TEST EXAMPLE 2

Now, the effects of the antiviral agent of the present invention for inhibition of the reverse transcriptase activities will be shown.

The test solution comprised magnesium chloride (5 mM), DTT (5 mM), sodium chloride (60 mM), [$^3$H]-TTP (0.2 mM), poly($\lambda$A) (10 μg/ml), Oligo (dT) (0.04 U/ml), reverse transcriptase derived from bird's myeloblastosis virus (3 U/ml) and Tris hydrochloric acid (pH 8.0). Compound 3 was dissolved in cyclodextrin to obtain a solution having a concentration of 5 mg/ml, which was then diluted with water to a predetermined concentration for use.

Then, 50 μl of the test solution and 50 μl of the sample solution were mixed, and the mixture was incubated at 37° C. for 60 minutes. Then, 50 μl of the incubated solution was sampled and soaked into a DEA filter paper. Then, this filter paper was washed with a 5% sodium monohydrogen phosphate solution and then with water and ethanol, followed by drying. The radioactivity contained in the captured fraction was measured by means of a scintillation counter. Then, the inhibition rate (%) of the sample Compound 3 was calculated from the radioactivity of the test sample group and that of the control group. The results are shown in Table 2.

TABLE 2

| Compound 3 (μg/ml) | Inhibition rate (%) |
| --- | --- |
| 10 | 57 |
| 5 | 34 |
| 2.5 | 11 |
| 1.25 | 6 |

Now, the present invention will be described in further detail with reference to Examples. However, it should be understood that the present invention is by no means restricted by such specific Examples.

EXAMPLE 1

Compound 3 (20 g) was suspended in 50 ml of a 5 w/v% polyoxyethylene hardened caster oil (HCO-60) aqueous solution and subjected to wet pulverization by Dino-mill (3,000 rpm for 45 minutes) using 50 g glass beads (diameter: 0.25–0.5 mm). After completion of the pulverization, glass beads were removed by a sieve to obtain wet-pulverized formulation of Compound 3. To 50 ml of this liquid formulation, 20 g of sucrose fatty acid ester (P1,670, manufactured by Mitsubishi Kasei Corporation) was added, and the mixture was freezed by dry ice.methanol and subjected to vacuum drying for 24 hours to remove water and obtain a freeze-dried formulation. This formulation was filled in capsules to obtain a capsule formulation.

EXAMPLE 2

Compound 3 (15 g) was suspended in 50 ml of a 5 w/v% polyoxyethylene polyoxypropylene glycol (Pluronic F68) aqueous solution and subjected to wet pulverization by Dino-mill (3,000 rpm for 45 minutes) using 50 g of glass beads (diameter: 0.25–0.5 mm). After completion of the pulverization, the glass beads were removed by a sieve to obtain a wet pulverized formulation of Compound 3.

To 50 ml of this liquid formulation, 30 g of sucrose fatty acid ester (P1,670, manufactured by Mitsubishi Kasei Corporation) was added, and the mixture was freezed by dry ice.methanol and then subjected to vacuum drying for 24 hours to remove water and obtain a freeze-dried formulation. This formulation was filled in capsules to obtain a capsule formulation.

EXAMPLE 3

A formulation was obtained in the same manner as in Example 2 except that instead of the polyoxyethylene polyoxypropylene glycol, decaglycerin monolaurate (Decaglin 1 L, manufactured by Nikko Chemical Company) was used.

EXAMPLE 4

Compound 3 (1.8 mg) was dispersed under heating in a suppository base material comprising 90% of polyethylene glycol 1000, 4% of polyethylene glycol 4000 and 6% of polyethylene glycol 400, and a suppository was prepared by means of a suppository mold.

EXAMPLE 5

Compound 3 (1.8 mg) was dispersed under heating in a Witep Sol W-35 suppository base material (about 45 mg) containing 12.5% (w/v) dimethyl $\beta$-cyclodextrin, to obtain a suppository.

EXAMPLE 6

Compound 3 was dissolved in polyethylene glycol 400 (PEG 400) to a concentration of 20 mg/ml, and soft gelatin capsules (average weight: 600 mg) were prepared in accordance with a usual method (Iyaku Kaihatsu Kisokouza XI "Methods for Preparation of Drugs" (jou), compiled by Tsuda Kyousuke et al., p. 347, published by Chijinshokan).

EXAMPLE 7

Soft gelatin capsules were prepared in the same manner as in Example 6 except that instead of PEG 400, purified soybean oil, purified sesame oil or purified safflower oil containing 5% (w/v) of Pluronic F31 was used.

EXAMPLE 8

A small amount of water was added to Compound 3 (4 g) and 125 g of dimethyl $\beta$-type cyclodextrin, and the mixture was kneaded and granulated by an extrusion granulation method, and then filled in hard gelatin capsules to obtain a capsule formulation for oral administration.

EXAMPLE 9

To the granular product obtained in Example 8, 1% of magnesium stearate was added, and the mixture was tabletted to obtain tablets for oral administration.

EXAMPLE 10

Compound 3 (50 mg), 500 mg of purified yolk phospholipid and 0.5 mg of $\alpha$-tocopherol were dissolved in 10 ml of chloroform, and the solution was heated under reduced pressure by means of a rotary evaporator to distill off chloroform and to obtain a thin film of a phospholipid containing Compound 3. To this thin film, 10 ml of a physiological sodium chloride solution was added, and immediately the mixture was shaked vigorously at room temperature for 20 minutes and then subjected to supersonic treatment for 1 hour under cooling with ice by means of a sonicator (Cell Distrutor #350, manufactured by Branson Sonic Power Company, output: 60 W). Then, centrifugal separation (25,000 g, 1 hour) at room temperature was conducted, and the precipitate at the lower most layer was recovered, centrifugally washed a few times by means of the above mentioned physiological sodium chloride solution, and then subjected to filtration for removal of bacteria, to obtain a phospholipid composite in a suspended state.

EXAMPLE 11

The suspended formulation obtained in Example 10 was subjected to freeze-dring to obtain 520 mg of a freeze dried formulation of the phospholipid composite.

EXAMPLE 12

Using Compound 3 (50 mg), treatment was conducted in the same manner as in Example 1. After filtration for the removal of bacteria, albumin (final concentration: 0.5%) was added, and the mixture was subjected to freeze-drying to obtain a formulation of a phospholipid composite.

EXAMPLE 13

The treatment was conducted in the same manner as in Example 1 except that in Example 1, Compound 1 was used instead of Compound 3, to obtain a capsule formulation.

EXAMPLE 14

The treatment was conducted in the same manner as in Example 1 except that in Example 1, Compound 2 was used instead of Compound 3, to obtain a capsule formulation.

EXAMPLE 15

The treatment was conducted in the same manner as in Example 1 except that in Example 1, Compound 4 was used instead of Compound 3, to obtain a capsule formulation.

EXAMPLE 16

The treatment was conducted in the same manner as in Example 1 except that in Example 1, Compound 5 was used instead of Compound 3, to obtain a capsule formulation.

EXAMPLE 17

The treatment was conducted in the same manner as in Example 1 except that in Example 1, Compound 6 was used instead of Compound 3, to obtain a capsule formulation.

What is claimed is:

1. A method for the treatment of viral infection comprising: administering to a mammal infected with a virus an effective amount of the benzoyl urea compound of the formula (I)

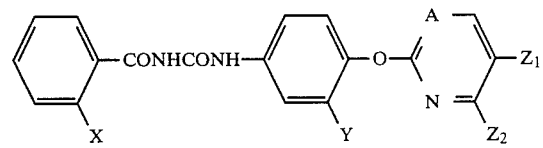

wherein X is a halogen atom or a nitro group; Y is a hydrogen atom, a halogen atom, a nitro group or a trifluoromethyl group; $Z_1$ is a halogen atom or a trifluoromethyl group; $Z_2$ is a hydrogen atom or a halogen atom; and A is CH or a nitrogen atom.

2. The method of claim 1 wherein the benzoyl urea compound is selected from the group consisting of: N-(2-chlorobenzoyl)-N'-[3-chloro-4-(5-trifluoromethyl-2-pyridinyloxy)phenyl]urea, N-(2-nitrobenzoyl)-N'-[3-chloro-4-(5-iodo-2-pyrimidinyloxy)phenyl]urea, N-(2-nitrobenzoyl)-N'-[3-chloro-4-(5-bromo-2-pyrimidinyloxy)phenyl]urea, N-(2-nitrobenzoyl)-N'-[3-chloro-4-(5-chloro-2-pyrimidinyloxy)phenyl]urea, N-(2-nitrobenzoyl-N'-3-trifluoromethyl-4-(5-chloro-2-pyrimidinyloxy)phenyl]urea and N-(2-nitrobenzoyl)-N'-[3-nitro-4-(5-chloro-2-pyrimidinyloxy)phenyl]urea.

3. The method of claim 1 wherein the benzoyl urea compound is selected from the group consisting of N-(2-nitrobenzoyl)-N'-[3-chloro-4-(5-iodo-2-pyrimidinyloxy)phenyl]urea, N-(2-nitrobenzoyl)-N'-[3-chloro-4-(5-bromo-2-pyrimidinyloxy)phenyl]urea and N-(2-nitrobenzoyl)-N'-[3-chloro-4-(5-chloro-2-pyrimidinyloxy)phenyl]urea.

4. The method of claim 1, wherein the benzoyl urea compound is N-(2-nitrobenzoyl)-N'-[3-chloro-4-(5bromo-2-pyrimidinyloxy)phenyl]urea.

5. The method of claim 1 wherein the benzoyl urea compound is N-(2-nitrobenzoyl)-N'-[3-chloro-4-(5-chloro-2-pyrimidinyloxy)phenyl]urea.

6. The method of claim 1 wherein the benzoyl urea compound is administered in the form of a composition including pharmaceutically acceptable excipients.

7. The method of claim 6 wherein said composition contains from 1 to 70% by weight of the benzoyl urea compound, from 1 to 30% by weight of a dispersant and from 1 to 90% by weight of a disintegrant.

8. The method of claim 1 comprising administering an effective amount of said benzoyl urea compound to an individual infected with at least one virus selected from the group consisting of herpesvirus, varicella zoster, cytomegalovirus, Epstein-Barr virus, picornavirus, togavirus, retrovirus, arenavirus, coronavirus, rhabdovirus, paramyxovirus, non-A-typed hepatitis virus, non-B-typed hepatitis virus, iridovirus, papovavirus, parvovirus, reovirus and bunyavirus.

* * * * *